United States Patent [19]

de Vries

[11] 4,122,266

[45] Oct. 24, 1978

[54] REACTION OF ARYL SULFONIC ACID ESTER AND AMINES

[75] Inventor: Louis de Vries, Greenbrae, Calif.

[73] Assignee: Chevron Research Company, San Francisco, Calif.

[21] Appl. No.: 644,474

[22] Filed: Dec. 29, 1975

Related U.S. Application Data

[63] Continuation-in-part of Ser. No. 585,281, Jun. 9, 1975, abandoned.

[51] Int. Cl.$^2$ .................. C07D 295/22; C07C 143/74; C10M 1/38
[52] U.S. Cl. ...................... 544/158; 252/33; 252/34; 252/47.5; 260/556 A; 260/556 AR; 548/351; 548/352; 544/398; 544/383
[58] Field of Search .......................... 252/33, 34, 47.5; 260/268 R, 556 A, 556 AR; 544/158

[56] References Cited

U.S. PATENT DOCUMENTS

| | | | |
|---|---|---|---|
| 2,236,168 | 3/1941 | Dietrich | 252/47.5 |
| 2,287,639 | 6/1942 | Pings | 252/47.5 X |
| 2,537,428 | 1/1951 | Séon et al. | 252/47.5 X |
| 2,740,814 | 3/1956 | Cross et al. | 252/47.5 X |
| 2,748,082 | 5/1956 | Zachar | 252/47.5 |
| 3,238,257 | 3/1966 | Ballard et al. | 44/72 |
| 3,287,267 | 11/1966 | Yonezaki et al. | 252/47.5 |
| 3,687,870 | 8/1972 | Muzyczko et al. | 260/556 AR X |
| 3,711,408 | 1/1973 | Karll et al. | 252/47.5 |
| 3,941,834 | 3/1976 | Lee | 252/47.5 X |

*Primary Examiner*—Daniel E. Wyman
*Assistant Examiner*—Thomas A. Waltz
*Attorney, Agent, or Firm*—C. J. Tonkin; L. L. Vaughan

[57] ABSTRACT

Oil-soluble, nitrogen-containing compositions, useful as lubricating oil additives, are provided. These compositions are prepared by reacting: (a) an aryl ester of a hydrocarbylethylsulfonic acid; or (b) a hydrocarbylsulfonyl chloride with a nitrogen-containing compound containing at least one amine hydrogen, i.e., —NH function. Also provided are processes for preparing these compositions and lubricating oil additive concentrates and lubricating oil compositions containing these compositions.

3 Claims, No Drawings

REACTION OF ARYL SULFONIC ACID ESTER AND AMINES

CROSS-REFERENCE TO RELATED APPLICATION

This application is a continuation-in-part of U.S. application Ser. No. 585,281, filed June 9, 1975, now abandoned the disclosure of which is hereby incorporated by reference.

BACKGROUND OF THE INVENTION

1. Field of the Invention

This invention pertains to new lubricating oil additives, processes for preparing them, lubricating oil additive concentrates containing them, and lubricating oil compositions containing these additives. More particularly, this invention relates to oil-soluble, nitrogen-containing compositions prepared from sulfonate esters or sulfonyl chlorides and primary or secondary amines.

Lubricating oil compositions, particularly for use in internal combustion engines, have long performed many functions other than simply lubricating moving parts. Modern-day, highly compounded lubricating oil compositions provide anti-wear, anti-oxidant, extreme-pressure and anti-rust protection in addition to maintaining the cleanliness of the engine by detergency and dispersancy. Many lubricating oil additives are well known for accomplishing these functions. For maintaining engine cleanliness, a well-known class of ashless detergents which have been found to be particularly useful are the amine reaction products of hydrocarbyl-substituted succinic acids, i.e., the well-known succinimides.

2. Description of the Prior Art

Dietrich, U.S. Pat. No. 2,236,168, teaches the use as detergents for lubricating oils of compounds of the formula $R(SO_2)NR'R''$ wherein R is an acyclic, alicyclic or aromatic radical and R' and R'' are hydrogen or alicyclic, aliphatic, heterocyclic or aromatic. The compounds are prepared by treating, for example, white oil, naphthenes, paraffin wax, etc., by conventional textbook processes, e.g., by reaction with sulfur dioxide and chlorine, to obtain random sites of sulfonation on the R group, which sites are then converted by conventional methods to the corresponding sulfonamide.

Knowles et al, U.S. Pat. No. 2,683,161, teach the stabilization, by heating to 110°–300° C., of aryl alkanesulfonates of the formula $R_1[SC_2-OR_2]x$, prepared from a saturated aliphatic hydrocarbon which has been reacted with (1) chlorine and sulfur dioxide, and (2) a phenol. In the above formula, $R_1$ is an aliphatic radical derived from a petroleum hydrocarbon containing saturated branched-chain hydrocarbons, preferably of 6 to 24 carbon atoms, and $R_2$ is phenyl. The compounds of this reference are disclosed as useful as plasticizers and functional fluids.

Distler, U.S. Pat. No. 3,133,948, discloses a process for preparing vinylsulfonates of aromatic hydroxy compounds. This process involves reacting carbyl sulfate with an aromatic hydroxy compound in an aqueous alkaline medium at a pH between 7.5 and 11.5 to yield a phenyl vinylsulfonate. Suitable aromatic hydroxy compounds include ortho- and para-chlorophenol. Carbyl sulfate is prepared from the reaction of ethylene with sulfur trioxide or oleum.

Klass et al., U.S. Pat. No. 3,158,639, state that carbyl sulfate has been known since 1836 and teach that it may be prepared by reacting ethylene with sulfur trioxide at a 1:2 mol ratio either in solution or in the vapor phase, usually at room temperature or lower to avoid charring.

Friedrichsen ard Distler, U.S. Pat. No. 3,205,249, disclose aryl esters of unsaturated sulfonic acids. The esters are prepared by reacting an olefin containing at least 1 methyl and/or methylene group adjacent to the double bond linkage with a vinylsulfonic acid aryl ester at temperature between 100°–300° C. Suitable olefins contain between 3 and 20 carbon atoms. The compounds of this reference are disclosed as useful as plasticizers and textile auxiliaries.

Ballard et al., U.S. Pat. No. 3,238,257, disclose N-tertiary-alkyl alkanesulfonamides of a formula $R-SO_2-NH-R^1$ useful in petroleum distillate fuels as anti-icing, anti-corrosion and carburetor detergency additives. In this formula, R is a saturated alkyl radical containing 12 to 30 carbon atoms and $R^1$ is a tertiary alkyl group having 8 to 22 carbon atoms. Preferred compounds contain a total of 25 to 35 carbon atoms between R and $R^1$. These sulfonamides are prepared by reacting an aliphatic hydrocarbon with gaseous sulfur dioxide and chlorine in the presence of actinic light to obtain a hydrocarbonsulfonyl chloride, which is then reacted with the desired amine. In a preferred embodiment, the aliphatic hydrocarbon is obtained from sulfochlorination of number 40 white oil, which is a highly acid-washed paraffin petroleum fraction having an average of 16 to 20 carbon atoms.

Stuart, U.S. Pat. No. 3,325,418, teaches a polysulfonamide-substituted polyclefin having a molecular weight of 200,000–1,000,000 which is prepared by treating the polyolefin with sulfur dioxide and chlorine gas to yield a product which is used for improving the viscosity index and as a detergent in lubricating oils.

Brasch, U.S. Pat No. 3,352,782, teaches amido sulfates of the formula

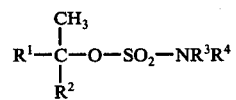

wherein $R^1$ is an organic group, $R^2$ is H or an organic group, and $R^3$ and $R^4$ are inter alia H or polyamine. These compounds, prepared by reacting an olefin polymer with chlorosulfonic acid and then with an amine, are useful as detergents in lubricating oil compositions.

SUMMARY OF THE INVENTION

In a first embodiment of this invention, there are provided oil-soluble, nitrogen-containing compositions, prepared by reacting: (a) an aryl ester of a substantially saturated hydrocarbylethylsulfonic acid, or (b) a substantially saturated hydrocarbylsulfonyl chloride with a nitrogen-containing compound containing at least one amine hydrogen, i.e., —NH function, in which the substantially saturated hydrocarbyl substituent contains at least 35 aliphatic carbon atoms. These compositions have excellent detergency and dispersancy properties in lubricating oils.

In a second embodiment, there are provided novel sulfonamides of the formula

wherein (a) $R^1$ represents a substantially saturated hydrocarbyl group containing about 35-350 carbon atoms and 0-3 sites of olefinic unsaturation;

(b) Q is a nitrogen-containing moiety derived by removing one or more hydrogen atoms from one or more nitrogen atoms of ammonia or an amine containing at least one primary or secondary amine group selected from hydrocarbylamine, aminohydrocarbylamine, alkoxyhydrocarbylamine, alicyclic hydrocarbylamine, alkylene polyamine, and heterocyclic amine; and (c) $m$ is a positive integer.

In a third embodiment, a process is provided for preparing these oil-soluble, nitrogen-containing compositions which comprises reacting the aryl ester of a substantially saturated hydrocarbylethylsulfonic acid with from about 0.1 to 15 mols per equivalent of said ester of nitrogen-containing compound containing at least one amine hydrogen, i.e., —NH function, at a temperature of 50° to about 250° C.

In a fourth embodiment, an additional process is provided for preparing these oil-soluble, nitrogen-containing compositions which comprises reacting a substantially saturated hydrocarbylsulfonyl chloride with from about 0.1 to 15 mols per equivalent of said chloride of a nitrogen-containing compound containing at least one amine hydrogen, i.e., —NH function, at a temperature from 10° to about 100° C.

In a fifth embodiment, lubricating oil additive concentrates comprise 90 to 10%w of an oil of lubricating viscosity and 10 to 90%w of an oil-soluble, nitrogen-containing composition prepared by reacting: (a) an aryl ester of a substantially saturated hydrocarbylethylsulfonic acid, or (b) a substantially saturated hydrocarbylsulfonyl chloride with a nitrogen-containing compound containing at least one amine hydrogen, i.e., —NH function, in which the substantially saturated hydrocarbyl substituent contains at least 20 aliphatic carbon atoms.

In a sixth embodiment, lubricating oil compositions comprise: (a) a major amount of an oil of lubricating viscosity, and (b) an amount effective to provide dispersancy of an oil-soluble, nitrogen-containing composition prepared by: (1) reacting an aryl ester of a substantially saturated hydrocarbylethylsulfonic acid or (2) a substantially saturated hydrocarbylsulfonyl chloride with a nitrogen-containing compound containing at least one amine hydrogen, i.e., —NH function, in which the substantially saturated hydrocarbyl subtituent contains at least 20 aliphatic carbon atoms.

The predominant organic group believed to be formed between the sulfonate ester or sulfonyl chloride group and the amine group is sulfonamide. Throughout the remainder of this discussion, the reaction products obtained as described in the first and second embodiments above will be generically described as sulfonamides, even though the reaction product comprises a mixture of sulfonamides, as illustrated by the second embodiment, with other reaction products.

The sulfonamides provided by this invention provide lubricating oil compositions having excellent detergency and dispersancy.

The sulfonamides of this invention are prepared from sulfonate esters or sulfonyl chlorides which are obtained from materials synthesized from readily available, inexpensive raw materials.

DETAILED DESCRIPTION OF THE INVENTION

In a first embodiment, oil-soluble, nitrogen-containing compositions comprise compositions prepared by: (a) reacting at a temperature from about 50° to about 250° C. an aryl ester of a substantially saturated hydrocarbylethylsulfonic acid, or (b) reacting at a temperature from 10° to 100° C. a substantially saturated hydrocarbylsulfonyl chloride, the substantially saturated hydrocarbyl substituent containing at least 35 aliphatic carbon atoms, with from 0.1 to 15 mols per equivalent of said ester or said chloride, of a nitrogen-containing compound containing at least one amine hydrogen, i.e., —NH function. The product ordinarily contains from 0.1-1.0 mol of the amine-derived portion of the product per equivalent of the sulfonate-derived portion.

In one preferred form of the first embodiment, the oil-soluble, nitrogen-containing compositions are prepared from an aryl ester of a substantially saturated hydrocarbylethylsulfonic acid having the hydrocarbyl substituent on either the alpha or beta carbon atom of the ethyl radical, or mixtures thereof, as in the following formulas:

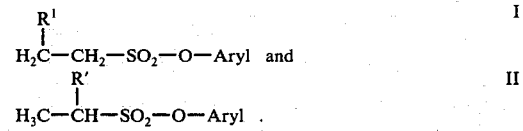

wherein $R^1$ represents a substantially saturated hydrocarbyl substituent containing a sufficient number of aliphatic carbon atoms to render the sulfonamide oil-soluble.

Generally $R^1$ will contain at least 35 and generally not moe than 350 carbon atoms, preferably from about 35 to about 250 carbon atoms and more preferably from about 50 to about 150 carbon atoms.

In a second preferred form of the first embodiment, the oil-soluble, nitrogen-containing compositions are prepared from a substantially saturated hydrocarbylsulfonyl chloride of the formula $R^1$—$SO_2$—Cl, wherein $R^1$ is as defined above.

The hydrocarbyl substituent preferably is substantially saturated. By "substantially saturated" is meant that at least about 95% of the total number of carbon-to-carbon covalent linkages are saturated linkages. An excessive proportion of unsaturated linkages renders the molecules susceptible to oxidation, degradation and polymerization and results in products unsuitable for use in hydrocarbon oils in many applications.

The substantially saturated hydrocarbyl substituent may contain polar substituents provided, however, that the polar substituents are not present in proportions sufficiently large to alter significantly the hydrocarbon character of the radical. Such polar substituents are exemplified by chloro, keto, alkyloxy, etc. The presence of such polar groups is not preferred, and the upper limit with respect to the proportion of such polar substituents in the radical is approximately 10%, based on the weight of the hydrocarbon portion of the radical.

The sources of the substantially saturated hydrocarbyl substituent include principally the high-molecular-weight, substantially saturated petroleums fractions and substantially saturated olefin polymers, particularly polymers of monoolefins having from 2 to about 30 carbon atoms. The especially useful polymers are the polymers of 1-monoolefins such as ethylene, propene, 1-butene, isobutene, 1-hexene, 1-octene, 2-methyl-1-heptene, 3-cyclohexyl-1-butene, and 2-methyl-5-propyl-1-hexene. Polymers derived from $C_2$–$C_5$ olefins are preferred. Polymers of olefins in which the olefinic linkage is not at the terminal position likewise are useful. Such olefins are illustrated by 2-butene, 3-pentene, and 4-octene.

Also useful are interpolymers of olefins such as those illustrated above with other interpolymerizable olefinic substances such as other 1-olefins, aromatic olefins, cyclic olefins, and polyolefins. Such interpolymers include, for example, those prepared by polymerizing isobutene with styrene, isobutene with butadiene, propene with isoprene, ethylene with piperylene, isobutene with chloroprene, isobutene with p-methyl styrene, 1-hexene with 1,3-hexadiene, 1-octene with 1-hexene, 1-heptene with 1-pertene, 3-methyl-1-butene with 1-octene, 3,3-dimethyl-1-pentene with 1-hexene, isobutene with styrene and piperylene, etc.

The relative proportions of the monoolefins to the other monomers in the interpolymers influence the stability and oil solubility of the final compositions derived from such interpolymers. Thus, for reasons of oil solubility and stability, the interpolymers contemplated for use in this invention should be substantially aliphatic and substantially saturated, i.e., they should contain at least about 80%, preferably about 95%, on a weight basis, of units derived from the aliphatic monoolefins and no more than about 5% of olefin linkages based on the total number of carbon-to-carbon covalent linkages. In most instances the percentage of olefinic linkages should be less than about 3% of the total number of carbon-to-carbon covalent linkages.

Specific examples of such interpolymers include copolymers of 95% (by weight) of isobutene with 5% styrene, terpolymer of 98% of isobutene with 1% of piperylene and 1% of chloroprene, terpolymer of 95% of isobutene with 2% of 1-butene and 3% of 1-hexene, terpolymer of 60% of isobutene with 20% of 1-pentene and 20% of 1-octene, copolymer of 80% 1-hexene and 20% of 1-heptene, terpolymer of 90% of isobutene with 2% of cyclohexene and 8% of propene, and copolymer of 80% of ethylene and 20% of propene.

The Aryl Hydrocarbylethylsulfonates

The hydrocarbon from the sources mentioned above can be adducted to the aryl vinylsulfonate by conventional techniques such as those used to adduct hydrocarbon substituents to maleic anhydride in the production of hydrocarbylsuccinic anhydrides. A fully satisfactory technique is to charge the hydrocarbyl substituent source to the reaction vessel and heat with stirring. The aryl vinylsulfonate is added to the reaction vessel and the reaction mass is heated to the reaction temperature at which it is held for the duration of the reaction. Generally reaction temperatures for the adduction reaction range from about 100°–300° C., preferably 150°–250° C. Generally the reaction will be carried out for about 1 to about 48 hours, preferably from about 2 to about 24 hours, at the preferred reaction temperatures. Generally it has been found that the reactivity of the hydrocarbyl substituent source in the adduction reaction can be enhanced if it is first chlorinated. For example, an excellent hydrocarbyl substituent source is chlorinated polyisobutene. In the adduction reaction, polyisobutenyl chloride reacts faster and at lower temperatures. The chlorine is substantially eliminated from the hydrocarbyl portion of the molecule during the reaction. Subsequent to the reaction, the adduct can be purified by conventional techniques such as extraction with a lower alkanol (e.g., methanol), followed by vacuum distillation to remove light ends from the product.

Alternatively the crude reaction mixture can be purified by codistillation with a hydrocarbon solvent at intermediate boiling range, such as a solvent-refined neutral oil. Preferably such a codistillation is carried out under reduced pressure, e.g., 100° C. at 2 mm Hg. Another method involves precipitation of insolubles by dilution with a lower-boiling hydrocarbon solvent, such as hexane, followed by decantation and stripping.

In the above formulas I and II, Aryl represents an aryl radical or a substituted aryl radical. The aryl substituent is obtained from aromatic hydroxy compounds which are reacted with carbyl sulfate to provide the aryl vinylsulfonate ester mentioned above. This ester is then adducted to the hydrocarbon to provide the hydrocarbyl-subtituted ethylsulfonic acid ester. The aryl substituent is not displaced during the adduction reaction.

Suitable aromatic hydroxy compounds which can be reacted with the carbyl sulfate to provide the aryl substituent contain at least one carbocyclic aromatic ring and at least one hydroxy group attached directly to a carbocyclic aromatic ring. In one embodiment, the aromatic ring is substituted with mild electron-withdrawing groups which promote its reactivity with the carbyl sulfate and also promote the reactivity of the adduct (hydrocarbylethylsulfonate) toward amines. Suitable electron-withdrawing groups are halo, e.g., chloro, bromo. A particularly useful group is a single chloro group located either ortho or para to the hydroxy group. The aromatic ring may also be substituted with mild electron-donating groups such as methyl, ethyl, and the like.

The preferred aromatic hydroxy compounds are those containing 1 to 3 carbocyclic aromatic rings and 1 to 3 hydroxy groups. If the aromatic hydroxy compound contains more than 1 aromatic ring, the rings may be condensed (as in naphthol), linked by a single bond (as in 4,4'-dihydroxydiphenyl) or linked via a short-chain bridge (as in 4,4'-dihydroxydiphenylmethane).

Suitable aromatic hydroxy compounds include phenol, the cresols, the xylenols, p-tertiary butylphenol, nonylphenol, dodecylphenols, c-chlorophenyl, p-chlorophenol, 4-chloro-2-methylphenol, 2,2'- or 3,3'-dimethyl-4,4'-dihydroxybiphenyl, 4,4-dihydroxydiphenylmethane, 2,2-bis-(4'-hydroxyphenyl)propane, bis-(4-hydroxyphenyl)sulfone, resorcinol, 3-cyanophenol, 4,4'-dihydroxydiphenyl sulfoxide, 3-iodophenol, octadecylphenol, 4-cyclohexylphenol, 4-cyclododecylphenol, 4-dibutylaminophenol, 4-(N-methyl-N-ethyl)aminophenol, 3-methoxyphenol, 4-butoxyphenol.

The aryl ester of vinylsulfonic acid can be prepared by several available techniques. One method, described in U.S. Pat. No. 3,121,730 to Distler, involves reacting a beta-chloro-ethanesulfonic acid chloride with phenol in an aqueous medium at a pH of between 7.5 and 11.5. The reaction proceeds with a loss of 2 mols of hydrogen chloride to yield phenyl vinylsulfonate. An alternative method, described in U.S. Pat. No. 3,133,948, also to Distler, involves reacting carbyl sulfate with an aromatic hydroxy compound in an aqueous alkaline medium at a pH between 7.5 and 11.5 to yield a phenyl vinylsulfonate.

Yet another method, which is more convenient than Distler's methods, does not allow the carbyl sulfate, once prepared, to solidify. This is particularly convenient, since solid carbyl sulfate is difficult to use. In this method the carbyl sulfate is prepared by reacting ethylene with sulfur trioxide at temperatures above the melting point of carbyl sulfate, about 110°–180° C., preferably about 160°–170° C. The molten carbyl sulfate is immediately introduced into an aqueous caustic solution of the aromatic hydroxy compound. The carbyl sulfate reacts with the aromatic hydroxy compound to yield the aryl ester of vinylsulfonic acid plus sodium sulfate. Preferably the aqueous solution is maintained between 0° C. and 25° C. After the sulfonate ester is isolated from the aqueous solution, it can be converted to the adduct as described above. The sulfonate esters are toxic, and care should be exercised in handling these materials.

The carbyl sulfate and the aromatic hydroxy compound usually react in equivalent quantities, i.e., a molar ratio of about 1:1 for monochydric phenols and about a 1:2 phenol/carbyl sulfate ratio for dihydric phenols. Since the carbyl sulfate tends to hydrolyze in the aqueous solution, an excess must be added in order to maintain a 1:1 equivalent ratio with the aromatic hydroxy compound.

The Hydrocarbylsulfonyl Chloride

The hydrocarbon from the sources mentioned above can be converted into the corresponding sulfonic acid or salt thereof by two distinct procedures.

In the first procedure, the hydrocarbon is reacted with a sulfonating agent, preferably chlorosulfonic acid. In the remainder of the discussion, the sulfonating agent will be referred to as chlorosulfonic acid for the sake of convenience.

In reacting chlorosulfonic acid with the hydrocarbon, subatmospheric, atmospheric and superatmospheric pressures may be employed. Pressure is not critical, and its selection is well within the skill of those in the art. Consequently, atmospheric pressure is usually employed as a convenience. It is preferred to react the chlorosulfonic acid and the hydrocarbon in the presence of a complexing diluent, such as an aliphatic ether or amide, such as diethyl ether, dibutyl ether, dimethyl formamide, dibutyl formamide, hexamethylphosphoramide, preferably containing from 2 to 8 carbon atoms. These compounds complex the chlorosulfonic acid to give a particularly advantageous reagent from the standpoint of improved yield. Noncomplexing solvents such as a mineral oil or a nonreactive organic solvent such as heptane, hexane, nitrobenzene, dichloroethane or various dichlorobenzenes may be used in addition to the complexing diluent. The purpose of these noncomplexing diluents is to aid in the handling of the various reactants and to more readily achieve a homogeneous reaction mixture. Benzene is not well suited for use as a diluent, since it tends to enter into side reactions.

If desired, the diluent may be omitted, although its use is preferred. Agitation of the reaction mixture is desirable. It is often convenient to use a slight molar excess of chlorosulfonic acid (based on 1 mol of polymer) to insure that the reaction between the hydrocarbon and the chlorosulfonic acid goes to completion. If the olefin polymer contains more than one unsaturated bond, one may introduce more than one sulfonic acid group into the polymer. In such a situation, a mol equivalent excess should be used (i.e., more than 1 mol of sulfonating agent per double bond). The amount of excess chlorosulfonic acid employed may vary widely, however, and will be a function of the amount of diluent employed as well as the desired rate of reaction. For example, it has been found that it is possible to employ substantially equal molar amounts of chlorosulfonic acid and hydrocarbon (e.g., polyisobutylene) and achieve substantially complete reaction. Where convenient, such a technique is preferred. Alternatively, 0.5 to 1.5 or 2 or 3 or even higher mol ratios of chlorosulfonic acid to hydrocarbon may be employed. Particularly preferred are substantially equal molar amounts of acid and polymer (on the basis of one double bond per polymer molecule). The temperature of reaction will generally be below 100° C., usually from 0° to 50° C. and more usually from about 15° to about 30° C. Preferably the reaction temperature is maintained below about 30° C., since the reaction is exothermic and quite vigorous. This feature, while desirable, is not critical. The reaction is characterized by hydrogen chloride evolution, which ceases shortly, especially if an excess of chlorosulfonic acid is employed. Reaction times will usually be on the order of 0.5 to 12 hours, e.g., 1 to 4 hours.

When the reaction is complete, it may be desirable to neutralize any excess chlorosulfonic acid (e.g., with $NaHCO_3$), and remove the neutralized acid by conventional techniques, e.g., filtration. If, however, essentially equal molar amounts of the acid and the olefin polymer have been employed, it is often convenient to continue the present process without any such neutralization and separation steps.

In an alternative preparation of the hydrocarbylsulfonic acid, the hydrocarbon is first reacted with an alkyl chlorosulfonate, optionally in the presence of a solvent such as 1,2-dichloroethane, ether, and the like. The reaction proceeds satisfactorily at temperatures from 40° to 120° C., preferably from 70° to 90° C., but below the decomposition point of the reactants and products. The reaction may be carried out at subatmospheric, atmoshperic or superatmospheric pressures; however, for the sake of convenience, the reaction is ordinarily conducted at atmospheric pressure.

The hydrocarbon and alkyl chlorosulfonate are ordinarily reacted using a slight molar excess of the sulfonate based on the hydrocarbon. Preferably from 1.1 to 2 mols of alkyl chlorosulfonate per mol of hydrocarbon is employed. It is preferred to run the reaction at a molar ratio of ester to olefin of 1.5 to 1 to insure the most efficient use of the reactants charged. The reaction is carried out in the presence of a high-boiling solvent, preferably a chlorinated hydrocarbon, which is inert to chlorosulfonic acid esters, for example 1,2-dichloroethane, chlorobenzene, dichlorobenzene, and the like.

The alkyl portion of the alkyl chlorosulfonate contains from 1 to 4 carbon atoms. Ethyl chlorosulfonate is preferred because it is easily prepared and reacts readily with hydrocarbon to yield an alkyl hydrocarbylsulfonate.

The alkyl chlorosulfonate is reacted with an olefin to yield an alkyl hydrocarbyl sulfonate which is then treated with a strong base, such as sodium methoxide, potassium methoxide, potassium hydroxide, and the like, at a temperature from 25° to 150° C., preferably 50° to 100° C., and a pressure of 1 to 10 atmospheres, in approximately equal molar proportions and in a lower alkanol ($C_1$ to $C_6$) solvent. This procedure yields a metal salt of the hydrocarbylsulfonic acid ester, for example, sodium hydrocarbylsulfonate.

The hydrocarbylsulfonic acid or salt prepared by either of the above procedures is then treated with a Vilsmeyer-Haack reagent, that is, an essentially 1:1 complex of a di-$C_1$-$C_4$ alkyl formamide such a dimethyl formamide and an inorganic chloride such as phosphorus cxychloride or thionyl chloride and the like to form the corresponding hydrocarbylsulfonyl chloride. It is often convenient to use a slight stoichiometric excess of the Vilsmeyer-Haack reagent; however, preferably approximately a 1:1 equivalent ratio of hydrocarbylsulfonic acid and Vilsmeyer-Haack reagent is employed.

The Amine

In a first embodiment the sulfonamide compositions are obtained by reacting: (a) the aryl ester of the substantially saturated hydrocarbylethylsulfonic acid or (b) a substantially saturated hydrocarbylsulfonyl chloride with a nitrogen-containing compound containing at least one amine hydrogen, i.e., —NH function. The amine hydrogen group must be present in order for the nitrogen-containing compound to react with the aryl ester or sulfonyl chloride to form the sulfonamide. A wide variety of nitrogen-containing compounds containing at least one amine hydrogen, i.e., —NH function, are suitable for use in preparing the sulfonamides of this invention. Suitable compounds include ammonia, aliphatic amines, and heterocyclic amines. The amines useful in preparing the sulfonamides discussed above have the formula

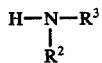

wherein $R^2$ and $R^3$ (A) each independently represent hydrogen or an organic radical bonded to the nitrogen through a carbon-to-nitrogen linkage such as hydrocarbyl, e.g., unsubstituted hydrocarbyl, aminohydrccarbyl, alkoxyhydrocarbyl, alicyclic hydrocarbyl and alkylene polyamine-substituted hydrocarbyl, or (B) together represent the remainder of a heterocyclic amine.

Preferably the aliphatic amines are selected from hydrocarbylamines, alkyoxy-substituted hydrocarbylamines, and alkylene polyamines. Specific examples of hydrocarbylamines include methylamire, propylamine, butylamine, pentylamine, hexylamine, heptylamine, octylamine, di-n-butylamine, di-n-hexylamine, decylamine, dodecylamine, hexadecylamine, octadecylamine, etc. Specific examples of alkoxy-substituted hydrocarbyl amines include methoxyethylamine, butoxyhexylamine, propoxypropylamine, heptoxyethylamine, etc., as well as the poly(alkoxy)amines such as poly(ethoxy)ethylamine, poly(propoxy)ethylamine, poly(propoxy)propylamine and the like.

Suitable examples of alkylene polyamines include, for the most part, alkylene polyamines conforming to the formula

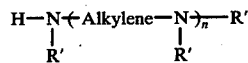   IV wherein (A) n is an integer preferably less than about 10: (B) each R' independently represents hydrogen or a substantially saturated hydrocarbon radical; and (C) each Alkylene radical can be the same or different and is preferably a lower alkylene radical having 8 or less carbon atoms, and when Alkylene represents ethylene, the two R' groups on adjacent nitrogen atoms may be taken together to form an ethylene group, thus forming a piperazine ring.

In a preferred embodiment, R' represents hydrogen, methyl or ethyl. The alkylene amines include principally methylene amines, ethylene amines, propylene amines, butylene amines, pentylene amines, hexylene amines, heptylene amines, ocytlene amines, other polymethylene amines, and also the cyclic and the higher homologs of such amines such as piperazines and amino-alkyl-substituted piperazines. These amines are exemplified specifically by: ethylene diamine, diethylene triamine, triethylene tetramine, propylene diamine, octamethylene diamine, di(heptamethylene) triamine, tripropylene tetramine, tetraethylene pentamine, trimethylene diamine, pentaethylene hexamine, di(trimethylene) triamine, 2-heptyl-3-(2-aminopropyl)imidazoline, 4-methylimidazoline, 1,3-bis(2-aminoethyl)imidazoline, 1-(2-aminopropyl)piperazine, 1,4-bis(2-aminoethyl)piperzine, and 2-methyl-1-(2-aminobutyl)piperazine. Higher homologs such as are obtained by condensing two or more of the above-illustrated alkylene amines likewise are useful.

The ethylene amines are especially useful. They are described in some detail under the healing "Ethylene Amines" in *Encyclopedia of Chemical Technology*, Kirk and Othmer, Vol. 5, pages 898–905, Interscience Publishers, New York (1950). Such compounds are prepared most conveniently by the reaction of an alkylene chloride with ammonia. The reaction results in the production of somewhat complex mixtures of alkylene amines, including cyclic condensation products such as piperazines. These mixtures find use in the process of this invention. On the other hand, quite satisfactory products may be obtained also by the use of pure alkylene amines. An especially useful alkylene amine for reasons of economy as well as effectiveness of the products derived therefrom is a mixture of ethylene amines prepared by the reaction of ethylene chloride and ammonia and having a composition which corresponds to that of tetraethylene pentamine.

Additional alkylene polyamines useful for preparing the sulfonamides of this invention include those of the following formulas:

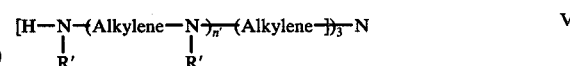   V

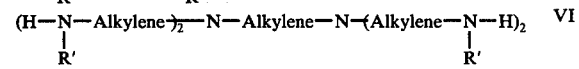   VI wherein
(a) n' is zero or an integer preferably less than about 10;
(b) each R' independently represents hydrogen or a substantially saturated hydrocarbon radical; and
(c) each Alkylene radical can be the same or different, and is preferably a lower alkylene radical having 8 or less carbon atoms, and when Alkylene represents ethylene, the two R' groups on adjacent nitrogen atoms in Formula IV may be taken together to form an ethylene group.

These amines are exemplified by tris-(aminoethyl)amine, N,N,N',N'-tetra(aminoethyl) ethylenediamine, and the like.

Suitable heterocyclic amines, in addition to the piperazines mentioned above in connection with the alkylene polyamines, include morpholines, imidazolines, aminoalkyl-substituted morpholines, and pyrrolidones such as aminoethyl pyrrolidone.

In a second embodiment of this invention, the products prepared from the aryl esters of the substantially saturated hydrocarbyl-substituted ethylsulfonic acid and a primary or secondary amine are believed to be primarily compounds of formulas VII and VIII below:

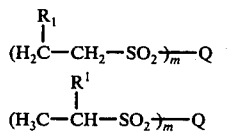

while the products prepared from the substantially saturated hydrocarbylsulfonyl chloride and a primary or secondary amine are believed to be primarily compounds of the formula

wherein
(a) $R^1$ represents a substantially saturated hydrocarbyl group containing about 35–350 carbon atoms and 0–3 sites of olefinic unsaturation;
(b) Q is a nitrogen-containing moiety derived by removing one or more hydrogen atoms from one or more nitrogen atoms of ammonia or an amine containing at least one primary or secondary amine group selected from hydrocarbylamine, aminchydrocarbylamine, alkoxyhydrocarbylamine, alicyclic hydrocarbylamine, alkylene polyamine, and heterocyclic amine; and
(c) $m$ is a positive integer.

Thus the Q group can be amino, hydrocarbylamino, aminohydrocarbylamino, alkoxyhydrocarbylamino, alicyclic hydrocarbylamino, alkylene polyaminehydrocarbylamino or heterocycloamino. When the amine is a monoamine, primarily a monosulfonamide ($n=1$) or sulfonimide ($m=2$) is formed. When the amine is a polyamine, each primary amine group is available for reaction with two aryl hydrocarbylethyl sulfonate groups and each secondary amine group is available for reaction with one aryl hydrocarbylethyl sulfonate group, thereby forming a mixture of mono-sulfonamides, bis-sulfonamides, tris-sulfonamides, etc., depending upon the relative molar proportions of amine and sulfonate. Preferred compounds are those wherein $m$ is one or two.

It is preferred that the group $R^1$ have either an alpha- or beta-carbon branched-chain configuration.

If a sulfonamide product having a completely saturated hydrocarbyl group is desired, it is necessary to hydrogenate the sulfonamide with hydrogen using a conventional noble metal or noble metal oxide hydrogenation catalyst, e.g., platinum or platinum oxide.

In a third embodiment of this invention, oil-soluble, nitrogen-containing compositions are prepared by reacting, at a temperature from about 50°–250° C., an aryl ester of a substantially saturated hydrocarbylethylsulfonic acid with a nitrogen-containing compound containing at least one amine hydrogen, i.e., —NH function.

In a fourth embodiment of the invention, oil-soluble, nitrogen-containing compositions are prepared by reacting, at a temperature from about 0° to 100° C., a substantially saturated hydrocarbylsulfonyl chloride with a nitrogen-containing compound containing at least one amine hydrogen, i.e., —NH function.

The aryl ester, the sulfonyl chloride and the nitrogen-containing composition have been described above. The oil-soluble sulfonamide product usually comprises from about 0.1 to about 1 mol of the amine-derived portion of the product per equivalent of the sulfonyl moiety in the product.

In order to drive the reaction to completion, generally an excess of amine, usually from about 1.1 to 15 mols of amine per equivalent of sulfonate ester or sulfonyl chloride, is used. The excess amine can later be recovered. By using excess amine, up to about 1 mol of monoamine can be reacted with the sulfonate ester or the sulfonyl chloride. However, up to about 1.5 mols of polyamine per equivalent of sulfonate ester can be incorporated, possibly by solubilization, into the sulfonamide composition.

As mentioned above, the reaction between the aryl hydrocarbylethylsulfonate and the amine is carried out at a temperature from about 50° C. to about 250° C., preferably from about 100° C. to about 200° C., and more preferably from about 125° C. to about 175° C. The reaction between the sulfonyl chloride and the amine is carried out at a temperature of 10° C. to 100° C.

Typically the aryl ester, sulfonyl chloride and the nitrogen-containing compound are liquids. Accordingly, the process can be conducted neat; however, suitable inert solvents can be used. Suitable solvents include hydrocarbons such as refined mineral oil, as well as lower-boiling aliphatic and aromatic hydrocarbons, particularly those which have boiling points at around the maximum temperature desired for the reaction mass.

Preferably the process is conducted under an inert atmosphere, nitrogen being the most inexpensive and readily available.

The process is usually conducted with stirring throughout the entire reaction time. Typically, heating and stirring are continued until the reactant present in the lesser equivalent amount is totally consumed. Ordinarily, the reaction takes place in about 1 to about 24 hours, and usually in about 2 to about 8 hours.

The excess of the reactants, as well as hydrogen chloride liberated during the reaction and any lower-boiling reaction solvents are removed by washing with bases, such as aqueous metal carbonates, methanolic bases, etc.

When the sulfonamide is prepared from the aryl hydrocarbylethylsulfonate, the excess reactants as well as the aromatic hydroxy compound can be removed by distillation.

Before this distillation operation, it is often desirable to sparge the reaction product with an inert gas such as nitrogen at elevated temperatures, e.g., about 150° C. to about 200° C., generally for several hours, e.g., 1 to 8 hours, to reduce the amounts of entrained aromatic hydroxy compound and excess amine in the reaction product. The sparging can be done under reduced pressure. Alternatively, undesirable products can be removed by codistillation with a hydrocarbon solvent of intermediate boiling range, such as a solvent-refined neutral oil. Preferably such codistillation is carried out under reduced pressure.

Subsequent to the sparging or codistillation operation, it is often desirable to dilute the reaction product with a suitable diluent in order to improve the handling characteristics of the reaction product. Typically about 25 to 50% weight diluent is added. Suitable diluents include solvent-refined neutral oils, particularly those having a low viscosity, e.g., about 100 SUS at 100° F. (37.8° C.).

In a fifth embodiment of this invention, lubricating oil additive concentrates are provided comprising from about 90 to about 10%w of an oil of lubricating viscosity and from about 10 to about 90%w of the oil-soluble, nitrogen-containing compositions prepared by reacting: (a) an aryl ester of a substantially saturated hydrocarbylethylsulfonic acid or (b) a substantially saturated hydrocarbylsulfonyl chloride with a nitrogen-containing compound containing at least one amine hydrogen, i.e., —NH function, in which the substantially saturated hydrocarbyl substituent contains at least 20 aliphatic carbon atoms. The concentrates provided by this embodiment of the invention should contain as much of the oil-soluble, nitrogen-containing composition as is practical, since the concentrates are prepared to reduce shipping costs, storage requirements, etc. Typically, the concentrates contain only sufficient diluent to make them easy to handle during shipping and storage. Suitable diluents for the concentrate include any inert diluent. Preferably the diluent is an oil of lubricating viscosity so that the concentrate may be readily mixed with lubricating oils to prepare lubricating oil compositions. Suitable lubricating oils which can be used as diluents typically have viscosities in the range from about 35 to about 1000 Saybolt Universal Seconds (SUS) at 100° F., although any oil of lubricating viscosity can be used.

In a sixth embodiment of this invention, lubricating oil compositions are provided which comprise: (a) an oil of lubricating viscosity; and (b) an amount effective to provide dispersancy of the oil-soluble, nitrogen-containing compositions prepared by reacting: (1) an aryl ester of a substantially saturated hydrocarbylethylsulfonic acid; or (2) a substantially saturated hydrocarbylsulfonyl chloride with a nitrogen-containing compound containing at least one amine hydrogen, i.e., —NH function, in which the substantially saturated hydrocarbyl substituent contains at least 20 aliphatic carbon atoms.

Suitable lubricating oils which can be used to prepare a lubricating oil composition or concentrate of this invention are oils of lubricating viscosity derived from petroleum or synthetic sources. The oils can be paraffinic, napththenic, halo-substituted hydrocarbons, synthetic esters, or combinations thereof. Oils of lubricating viscosity have viscosities in the range of 35 to 50,000 SUS at 100° F., and more usually from about 50 to 10,000 SUS at 100° F. The amount of the oil-soluble, nitrogen-containing composition of this invention which is incorporated into the lubricating oil to provide the effective amount necessary for dispersancy varies widely with the particular sulfonamide used as well as the use intended for the lubricating oil composition. Other conventional additives which can be used in combination with the sulfonamides, include ashless dispersants such as the type disclosed in U.S. Pat. Nos. 3,172,892, 3,219,666, 3,381,022; neutral and basic calcium, barium and magnesium petrosulfonates or alkyl phenates; oxidation inhibitors, antifoam agents, viscosity index improvers, pour-point depressants, and the like, such as chlorinated wax, benzyldisulfide, sulfurized sperm oil, sulfurized terpene; phosphorus esters such as trihydrocarbon phosphites and phosphates; metal thiocarbamates such as zinc dioctyldithiocarbamate; metal phosphorus dithioates such as zinc dioctylphosphorodithioate; polyisobutene having an average molecular weight of 100,000; etc.

In general, the lubricating oil compositions will contain from about 0.1 to about 20%w of said oil-soluble, nitrogen-containing composition. More usually, the lubricating oil composition of the invention will contain from about 0.5 to about 10%w of the nitrogen-containing composition and more usually from about 1 to about 8%w of the nitrogen-containing composition.

Alternatively, the lubricating oil composition can be prepared by combining: (a) a composition comprising a major amount of an oil of lubricating viscosity and a dispersant amount of said oil-soluble, nitrogen-containing composition; and (b) a concentrated lubricating oil additive composition comprising an oil of lubricating viscosity and up to 90%w, but at least a dispersant amount, of said oil-soluble, nitrogen-containing composition.

The lubricating oil compositions of the invention are useful for lubricating internal combustion engines. The lubricating oils not only lubricate the engine, but, because of their dispersancy properties, help maintain a high degree of cleanliness of the lubricated parts.

Those lubricating oils containing sulfonamides of this invention wherein the $R^1$ group contains from 20 to about 35 carbon atoms are useful in particular as lubricants in 2-cycle engines.

The sulfonamides of this invention find additional utility as fuel additives in which capacity from 0.00001 to 5%w sulfonamide is employed. When employed in normally liquid petroleum distillate fuels, e.g., fuel oils, diesel oils, gasolines, aviation gasoline, jet fuels, etc., they promote engine cleanliness, particularly of the fuel system, such as fuel lines, carburetors, injectors, pumps and the like. In furnace fuel oils, for example, they serve as anti-screen-clogging agents.

The following examples are included to further illustrate the invention.

EXAMPLES

EXAMPLE 1A

Preparation of c-chlorophenyl vinylsulfonate

A 5-liter, four-neck flask is equipped with an electric motor-driven stirrer, thermometer and Y tube. A water-cooled condenser is inserted into one branch of the Y tube. The outlet of the condenser is connected to a bubbler. A pressure-compensated dropping furrel containing a 25% solution of sodium hydroxide in water is inserted into the other branch of the Y tube. A 500-ml, four-neck flask is fitted with a bottom outlet. This outlet is inserted into the fourth neck of the 5-liter flask by way of a 15 inch gooseneck adaptor. This gooseneck adaptor is wrapped with electrical heating tape which heats the outlet to about 115°–125° C. The 500-ml flask is equipped with an electric motor-driven stirrer, a thermometer, an ethylene gas inlet and a Y tube. A thermometer is inserted into one branch of the Y tube. The other branch of the Y tube is outfitted with a pressure-compensated dropping funnel. The opening of the top of the dropping funnel is fitted with a nitrogen gas inlet tube. The gas inlet tube is connected to a bubbler unit, which in turn is connected to a compressed nitrogen supply.

The 5-liter flask is charged with 1280 ml of water, 640 ml of 1,2-dichloroethane, 150 ml of 25% sodium hydroxide in water, and 350 g (2.72 mols) of o-chlorophenol. This mixture is stirred and cooled to 0° C. in a dry ice-acetone bath. The dropping funnel of the 500-ml flask is charged with the contents of a 2-lb (908 g) ampule of sulfur trioxide. Even though the sulfur trioxide contains an inhibitor, typically commercial ampules contain a small amounts of polymerized sulfur trioxide. A 2-lb ampule in good condition typically contains 850–860 g of liquid sulfur trioxide. The heating tape for the gooseneck adaptor and stirrer for the 500-ml flask are turned on and the entire reaction system is blanketed with nitrogen, which is introduced via the sulfur trioxide dropping funnel from the nitrogen bubbler. After the reaction system is filled with nitrogen, ethylene is introduced into the 500-ml flask via the gas inlet tube. After the ethylene flow is established, sulfur trioxide is introduced into the reaction vessel from its addition funnel. The stirrer in the 500-ml flask causes intimate mixing of the ethylene and the sulfur trioxide. The reaction between ethylene and sulfur trioxide rapidly takes place with evolution of heat of reaction to yield carbyl sulfate. The heat of reaction quickly warms the reaction vessel to approximately 150°–170° C. At these temperatures, the carbyl sulfate, which has a melting point of about 109°–110° C., remains liquid and runs down the heated bottom outlet tube and drops into the stirrer sodium chlorophenate solution in the 5-liter flask.

The carbyl sulfate and sodium chlorophenate react under alkaline conditions (pH 9–11) to yield o-chlorophenyl vinylsulfonate and sodium sulfate.

The flow rate of the ethylene is adjusted such that there is a slight excess over that necessary to react with the sulfur trioxide introduced from the dropping funnel. This is readily determined by comparing the bubbling rate in the bubbler attached to the sulfur trioxide addition funnel and the bubbler attached to the outlet of the condenser on the 5-liter flask. A slight excess of ethylene is obtained when the bubbler rate on the condenser is faster than on the inlet of the sulfur trioxide addition funnel. The reaction is continued until all of the sulfur trioxide has been consumed. Periodically throughout the reaction, the pH of the reaction mass in the 5-liter flask is checked. Sodium hydroxide is added from its addition funnel continuously to maintain the pH between 9 and 11.

After the sulfur trioxide is consumed, the reaction mass in the 5-liter flask is stirred for about 30 minutes and then neutralized with concentrated HCl to pH 5. The reaction mass is then heated to 40° C. and transferred to a separatory funnel. The organic layer is drained off, filtered through Celite filter aid and stripped of all light ends on a rotary evaporator to an end point of 100° C. at 2 to 5 mm Hg. Typical crude yields of o-chlorophenyl vinylsulfonate from a 350-g charge of o-chlorophenol vary from 550 to 615 g. Typically, the crude product contains less than 1% unreacted o-chlorophenol, and has 15.3–16.4% sulfur, 15.0–15.6% chlorine.

EXAMPLE 1B

Preparation of phenyl vinylsulfonate

Using the same apparatus and the same procedure, phenyl vinylsulfonate is prepared from a charge of 253 g of phenol in the 5-liter reaction flask. Analysis: 14.8–15.4% S.

EXAMPLE 2

Adduction of o-chlorophenyl vinylsulfonate to polybutene

A reaction kettle is equipped with a stirrer, thermocouple dip tube, cold-water-jacketed riser and condenser, a gas inlet, and a charge port.

9.87 kg (10.39 g-mols) of a polybutene having a number average molecular weight of 950 is charged to the kettle under a nitrogen blanket. With stirring, the charge is heated to 120° C. 2.73 kg (12.47 g-mols) of o-chlorophenyl vinylsulfonate is added from an addition funnel through the charge port. With stirring, the reaction mass is heated to 220° C. and held at this temperature for 24 hours while the nitrogen atmosphere is maintained and cooling is maintained in the condenser.

At the end of 24 hours the reaction mass is cooled to less than 65° C. and 15 liters of methanol are added. The mass is heated to reflux at approximately 65° C. with stirring and still under the nitrogen atmosphere. The mass is refluxed for 45 minutes and then cooled to room temperature. Agitation is stopped and phase separation is allowed to take place. If place separation does not occur readily, another 4 to 8 liters of methanol can be added.

The bottom layer is withdrawn from the reaction kettle and saved. The top layer is transferred to a storage tank. The bottom layer is returned to the kettle and another 15 liters of methanol are added to the kettle. The reaction mass is heated to reflux for 45 minutes with agitation, then cooled at room temperature and allowed to separate. The bottom layer is withdrawn from the kettle and the top layer is transferred to the storage vessel. The bottom layer is returned to the kettle and the container it was in is rinsed with 4 liters of hydrocarbon thinner which is added to the kettle. The riser to the condenser is heated to 82° C., but cold water is maintained on the heat exchanger. A vacuum is applied to the kettle and the contents are heated to 165° C. maximum to distill off the thinner and methanol. The bottoms are cooled to room temperature and transferred to a storage container. The chlorophenyl polybutene-substituted ethylsulfonate thus obtained is satisfactory for preparing the sulfonamides of this invention without further purification. Typical analysis: %S=1.46–1.54, %Cl=1.49–1.56.

EXAMPLE 3

Adduct of polyisobutenyl chloride and chlorophenyl vinylsulfonate

EXAMPLE 3A 512 g (0.357 mol) of a polyisobutenyl chloride (4%w chlorine) prepared from a polyisobutene having a number average molecular weight of 1400, and 94 g (0.43 mol) o-chlorophenyl vinylsulfonate are charged to a 1-liter, four-neck flask equipped with a stirrer, thermometer and nitrogen gas inlet. While maintaining a nitrogen atmosphere, the reaction mixture is heated with stirring at 210° C. and maintained at that temperature for 7 hours. 16-ml samples are taken at 2, 4 and 7 hours for Hyamine titrations.

The Hyamine titration is used to determine the amount of anionic detergent in a sample. A known weight of sample is dissolved in chloroform and titrated with a dilute aqueous solution of Hyamine 1622. Acidic methylene blue is used as an indicator. The Hyamine solution is added in suitable increments with 2 minutes of vigorous shaking after each addition. The blue color is at first concentrated in the lower (chloroform) layer, but gradually appears in the upper (aqueous) layer as the Hyamine is added. The end point is taken as that point at which the color in the two layers is equal. The millimcls of sulfonate per gram of sample are equal to VM/W, where V is the milliliters of Hyamine solution, M is the molarity of the Hyamine solution, and W is the grams of sample.

At the end of 7 hours, the remainder of the reaction mixture (532 g) is cooled and transferred to a 2-liter, three-neck flask equipped with a stirrer and a thermometer, using 50 ml of a hydrocarbon thinner to flush the reaction flask. To the product/thinner mixture, 800 ml of methanol are added and the mixture is stirred at reflux (64° C) for 45 minutes. An emulsion is obtained which does not break on standing. An additional 200 ml of methanol and 200 ml of hydrocarbon thinner are added and the mixture is stirred for 2 minutes. The mixture is then allowed to settle at ambient temperature for 1.5 hours and the supernatant liquid (ca. 1100 ml) is decanted. 800 ml of methanol is added to the mixture remaining in the flask and stirred at reflux (63° C.) for 45 minutes. Again, an emulsion is obtained. 200 ml of the hydrocarbon thinner is added and the mixture is stirred for 2 minutes. The mixture is then allowed to settle at ambient temperature for 1.5 hours and the supernatant liquid (ca. 800 ml) is decanted. The extracted product remaining in the flask is dissolved in hydrocarbon thinner and transferred to a 1-liter, three-neck flask with a small amount of solvent; the solvent is stripped off to an end point of 165° C. at 5 mm Hg to yield 466 g of product. Analysis: S, 0.88%w; Cl 1.19%w.

EXAMPLE 3B

The same apparatus is used as in Example 3A. 512 g (0.357 mol) of a polyisobutenyl chloride (4%w chlorine prepared from a polyisobutene having a number average molecular weight of 1400), and 97 g (0.43 mol) o-chlorophenyl vinylsulfonate are charged to the flask. The reaction mixture is heated with stirring at 180° C. for 10 hours while maintaining a flow of nitrogen through the flask. The off-gas is scrubbed through a sparger into an Erlenmeyer flask containing 200 ml water. 16-ml samples are withdrawn at 2, 4, 6 and 10 hours for Hyamine titration. The off-gas water trap is replaced each time a sample is taken. The water is titrated to a methyl organe end point with 3N-sodium hydroxide solution. The 4 titrations require 100, 32.3, 19 and 20.4 ml, respectively, for a total of 171.7 ml, which is equivalent to 0.515 mol of sodium hydroxide.

The remainder of the reaction mixture (530 g) is transferred to a 2-liter, three-neck flask using about 50 ml of hydrocarbon thinner to rinse the reaction flask. 800 ml of methanol is added to the three-neck flask and the mixture is refluxed with stirring for ¾ hour. Complete separation is not obtained upon cessation of stirring. 200 ml of n-hexane is added and the mixture is stirred for 2 minutes. After the mixture settles at ambient temperature for 1 hour, approximately 800 ml of supernatant liquid is decanted. 800 ml of methanol is added to the 2-liter flask and the mixture is refluxed for ¾ hour. After standing at ambient temperature for 1.5 hours, about 900 ml of supernatant liquid is decanted. The mixture remaining in the flask is dissolved in hydrocarbon thinner and transferred to a 1-liter, three-neck flask. The solvent is stripped off the product to an end point of 165° C. at 5 mm Hg to yield 460 g of product. Analysis: S, 0.99%w, Cl, 1.84%w.

EXAMPLE 3C

To a 1-liter, four-neck flask equipped as in Example 3A above, 506 g 0.5 mol) of polybutene chloride (4%w chlorine) prepared from a polyisobutene having a number average molecular weight of 950 is added under a nitrogen atmosphere. 142 g (0.65 mol) of o-chlorophenyl vinylsulfonate is then added. The reaction mass is heated with stirring at 210° C. for 7 hours while maintaining a nitrogen atmosphere in the flask. 16-ml samples are withdrawn at 2, 4 and 7 hours for Hyamine titration in order to follow the progress of the reaction. At the end of the 7-hour reaction period, the remainder of the reaction mixture (569 g) is transferred to a 2-liter, three-neck flask using about 50 ml of the hydrocarbon thinner to rinse the reaction flask. 800 ml of methanol is added to the flask and the mixture is stirred at reflux (64° C.) for about 45 minutes. The mixture is allowed to stand at ambient temperature for about 3½ hours. Fast separation is obtained, but only about 700 ml of supernatant liquid could be decanted. 800 ml of methanol is added and the mixture is stirred at reflux (64° C.) for about 45 minutes. The mixture is allowed to stand at ambient temperature for 1¾ hours. Fast separation is again obtained, but only about 500 ml of supernatant liquid can be decanted. 600 ml of n-hexane is added to the flask and the mixture is stirred for 2 minutes. After settling for ¼ hour, about 550 ml of supernatant liquid is siphoned off. The mixture remaining in the flask is transferred to a 1-liter, three-neck flask using a small amount of n-hexane to rinse the flask. The solvent is removed by stripping at 190° C. at 5 mm Eg to yield 475 g of product. analysis: S, 1.80%w; Cl 2.16%w.

EXAMPLE 4

A general procedure of synthesis of sulfonamides

A flask is fitted with a thermometer, stirrer and reflux condenser. The flask is charged with the aryl ester of the hydrocarbyl-substituted ethylsulfonic acid. The amine is then added and the mixture is placed under a nitrogen atmosphere, heated with stirring to the temperature and for the time indicated below. Excess amine and the aracmtic hydroxy compound liberated during the reaction are removed by distillation at subatmospheric pressures (generally about 1-2 mm Hg) to an end point of about 170° C. The residue is then sparged with nitrogen at 170° C., typically for about 6-8 hours, to reduce the amount of entrained aromatic hydroxy compounds. The final product is diluted with a neutral solvent-refined lubricating oil having a viscosity of 100 SUS at 100° F. to improve its handling characteristics (typically 25-33%w diluent oil is used).

In the following Examples A-W, sulfonamides are prepared from the c-chlorophenyl ester of a polyisobutenylethylsulfonic acid. The polyisobutenyl group has a number average molecular weight of about 950.

Example A—From n-hexylamine 25 g of chlorophenyl polyisobutenylethylsulfonate (1.69%w sulfur) is reacted with 12.7 g (9.5 equivalent ratio) of n-hexylamine for 4 hours at 115° C. The product is stripped under vacuum and sparged with nitrogen for 8 hours at 170° C. to yield 23.4 g of product. The product is diluted with 7.8 g of a 100 SUS neutral solvent-refined lubricating oil. Analysis: Cl, 0.07%w; S, 1.17%w; N, 0.53%w.

Example B—From n-heptylamine 25.1 g of chlorophenyl polyisobutenylethylsulfonate (1.77%w sulfur) is reacted with 8.20 g (5.1 equivalent ratio) of n-heptylamine for 4 hours at 166° C. (reflux). The sulfonate was previously dried by using a benzene azeotrope and the amine was dried over calcium hydride. The reaction product is stripped under vacuum and sparged with nitrogen to yield 24.0 g. The product is diluted with 8.0 g of a 100 SUS neutral solvent-refined lubricating oil. Analysis: Cl, 0.24%w; S, 1.29%w; N, 0.51%w.

Example C—From n-octylamine 409.9 g of chlorophenyl polyisobutenylethylsulfonate (1.62%w sulfur) and 280.1 g (10.5 equivalent ratio) of n-octylamine are reacted at 160° C. for 3 hours. The reaction product is stripped under vacuum and sparged with nitrogen to yield 400.8 g of product. The product is diluted with 133.6 g of a 100 SUS neutral solvent-refined lubricating oil. Analysis: Cl, 0.07%w; S, 1.25%w, N, 0.53%w.

Example D—From di-n-butylamine 25.0 g of the sulfonate used in Example B and 14.0 g (7.9 equivalent ratio) of di-n-butylamine are reacted at 170° C. (reflux) for 4 hours. The product is stripped under vacuum and sparged with nitrogen for 10 hours at 170° C. to yield 22.8 g of product. The product is diluted with 7.6 g of a 100 SUS neutral solvent-refined lubricating oil. Analysis: Cl, 0.12%w; S, 1.03%w; N, 0.32%w.

Example E—From di-n-hexylamine 25.1 g of the sulfonate used in Example B and 7.5 g (2.9 equivalent ratio) of di-n-hexylamine are reacted at 180° C. (reflux) for 22 hours. The reaction mass is stripped under vacuum and sparged with nitrogen to yield 22.5 of product. The product is diluted with 7.5 g of a 100 SUS neutral solvent-refined lubricating oil. Analysis: N, 0.33%w.

Example F—From morpholine 25.0 g of the sulfonate used in Example B and 5.4 g (4.5 equivalent ratio) of morpholine are reacted at 150° C. for 28 hours. The sulfonate previously was dried with a benzene azeotrope prior to use. The reaction mass is stripped under vacuum to yield 23.6 g of product. The product is diluted with 7.9 g of a 100 SUS neutral solvent-refined lubricating oil. Analysis: Cl, 0.42%w; S, 1.41%w; N, 0.46%w.

Example G—From piperazine 2055 g chlorophenyl polyisobutenylethylsulfonate (1.56%w sulfur) prepared as in Example 2 and 257 g (3 mol ratio) of piperazine are reacted at 130° C. (reflux) for 4 hours. The reaction mass is diluted with 0.5% volume is mixed hexanes, vacuum-filtered through Celite 545, stripped under vacuum, and sparged with nitrogen for 18 hours to yield 1927 g of product. The product is diluted with a 100SUS neutral solvent-refined lubricating oil. Analysis: Cl, 0.084%w; S, 1.52%w; N, 1.08%w.

Example H—From 1,3-propanediamine 2055 g of the sulfonate used in Example G and 371 g (5 mol ratio) of 1,3-propanediamine are reacted at 152° C. (reflux) for 4 hours. The reaction mass is diluted with 0.5% vol. of mixed hexanes, vacuum-filtered through Celite 545, stripped under vacuum, and sparged with nitrogen for 6 hours to yield 1934 g of product. Analysis: Cl, 0.03%w; S, 1.43%w; N, 2.81%w.

Example I—From 1,6-hexanediamine 30 g of the sulfonate used in Example H and 16.5 g (10 mol ratio) of 1,6-hexanediamine are reacted at 140° C. for 2 hours. The reaction mass is stripped under vacuum and sparged with nitrogen for 4 hours to yield 29.2 g of product. The product is diluted with 9.7 g of a 100 SUS neutral solvent-refined lubricating oil. Analysis: Cl, 0.024%w; S, 1.08%w; N, 0.88%w.

Example J—From dimethylaminopropylamine 25.0 g of the sulfonate used in Example H and 12.0 g (9.9 mol ratio) of dimethylaminopropylamine are reacted at 125° C. (reflux) for 2 hours. The reaction product is stripped under vacuum and sparged with nitrogen to yield 24 g of product. The product is diluted with 8.0 g of a 100 SUS neutral solvent-refined lubricating oil. Analysis: Cl, 0.12%wt; S, 1.14%w; N, 0.89%w.

Example K—From tris-(2-aminoethyl)amine 50 g of the sulfonate used in Example H and 40 g (11.6 mol ratio) of tris-(2-aminoethyl)amine are reacted at 130° C. for 2 hours. The reaction mass is stripped under vacuum and sparged with nitrogen to yield 46.5 g of product. The product is diluted with 15.5 g of a 100 SUS neutral solvent-refined lubricating oil. Analysis: Cl, 0.036%w; S, 1.25%w; N, 1.21%wt.

Example I—From ethylenediamine 1580 g of chlorophenyl polyisobutenylethylsulfonate (1.52%w sulfur) prepared as in Example 2 and 483 g (12 mol ratio) of ethylenediamine are reacted at 120° C. (reflux) for 4 hours. The reaction mass is stripped under vacuum and sparged with nitrogen for 5 hours to yield 1522 g of product. The product is diluted with a 100 SUS neutral solvent-refined lubricating oil. Analysis: Cl, 0.02%w; S, 1.24%w; N, 1.15%w.

Example M—From ethylenediamine

The sulfonate is dried by benzene azeotrope and the ethylenediamine is dried over potassium hydroxide. 400.3 g of o-chlorophenyl polyisobutenylethylsulfonate (1.50%w sulfur) and 120.8 g (10.7 mol ratio) of ethylenediamine are reacted at 124° C. (reflux) for 4 hours. The reaction product is stripped under vacuum and sparged with nitrogen for 5 hours at 175° C. to yield 354.9 g of product. The product is diluted with 118.3 g of a 100 SUS neutral solvent-refined lubricating oil. Analysis: Cl, 0.086%w; S, 1.21%w N, 0.95%w.

Example N—From diethylenetriamine 2105 g of the sulfonate used in Example 4I and 309 g (3 mol ratio) of diethylenetriamine are reacted at 160° C. for 6 hours. The reaction mass is stripped under vacuum, sparged with nitrogen for 6 hours, diluted with 0.5% vcl. of mixed hexanes, vacuum filtered through Celite 545, and stripped under vacuum to yield 1952 g of product. The product is diluted with a 100 SUS neutral solvent-refined lubricating oil. Analysis: Cl, 0.86%w, S, 1.18%w, N, 1.60%w.

Example C—From triethylenetetramine 65.3 g (30 mmols) of o-chlorophenyl polyisobutenylethylsulfonate and 2.2 g (15 mmols) of triethylenetetramine are reacted at 200° C. The reaction mass is then stripped to an end point of 1.5 mm Hg at 200° C., and held at those conditions for ¼ hour, to yield 64.0 g of product. The product is diluted with 21.3 g of a 100 SUS neutral solvent-refined lubricating oil. Analysis: Cl, 0.24%w; S, 1.07%w; N, 1.0%w.

Example P—From triethylenetetramine 2050 g of the sulfonate used in Example 4I and 71 g (0.5 mol ratio) of triethylenetetramine are reacted at 180° C. for 6 hours. The reaction mass is diluted wtih 0.5% vol. of mixed hexanes, vacuum filtered through Celite 545, stripped under vacuum, and sparged with nitrogen for 6 hours to yield 1939 g of product. The product is diluted with a 100 SUS neutral solvent-refined lubricating oil. Analysis: Cl, 0.081%w; S, 1.13%w; N, 1.18%w.

Example C—From tetraethylenepentamine 2411 g of chlorophenyl polyisobutenylethylsulfonate (1.33%w sulfur) and 378 g (2 mol ratio) of tetraethylenepentamine are reacted at 100° C. for 8 hours. The reaction mass is diluted with 1.5 vol. of kerosene, allowed to settle for 6 days, stripped under vacuum, diluted to 50%w concentration with a 100 SUS neutral solvent-refined lubricating oil, and vacuum filtered through Celite 545 to yield 4811 g of product. The product is diluted with a 100 SUS neutral solvent-refined lubricating oil. Analysis: S, 0.62%w; N, 1.79%w.

Example R—From tetraethylenepentamine 2055 g of the sulfonate used in Example 4G and 379 g (2 mol ratio) of tetraethylerepentamine are reacted at 200° C. for 6 hours. The reaction mass is diluted with 0.5% vcl. of mixed hexanes, vacuum filtered through Celite 545, stripped under vacuum, and sparged with nitrogen for 5.5 hours to yield 2087 g of product. The product is diluted with a 100 SUS neutral solvent-refined lubricating oil. Analysis: Cl, 0.04%w; S, 1.03%w; N, 3.11%w.

Example S—From ammonia 1262 g of sulfonate similar to that prepared in Example 2 is charged to a 1-gallon autoclave at room temperature. A total of 864 g liquid ammonia is added at 130 psig. The reaction mixture is stirred and heated to 125° C. over 1.5 hours at 1400 psig. The mixture is cooled to room temperature. Excess ammonia is vented. The crude product (1187 g) is drained, heated and sparged with nitrogen for 24 hours. The product is diluted with a 100 SUS neutral solvent-refined lubricating oil. Analysis: Cl, 0.07%w; S, 1.91%w; N, 0.76%w.

Example T—From bis-N,N'-aminopropylethylenediamine 1446 g of the sulfonate used in Example 4C and 288 g (3 mol ratio) of bis-N,N'-aminopropylethylenediamine are reacted at 100° C. for 8 hours. The reaction mass is diluted with 2.5% vol. of mixed hexanes, allowed to settle for 2 days, vacuum filtered through Celite 545, stripped under vacuum, diluted with 1.5 vol. kerosene, stripped under vacuum, and diluted to 50%w concentration with a 100SUS neutral solvent-refined lubricating oil. Analysis: S, 0.60%w; N, 1.35%w.

Example U—From the monosulfonamide of piperazine 16.45 g of the sulfonate used in Example 4B is reacted with 18.26 g (1.14 mol ratio) of the monosulfonamide of piperazine. The reaction is continued for 22 hours at 150° C. The reaction mass is stripped under vacuum and sparged with nitrogen to yield 31.2 g of product. The product is diluted with 10.4 g of a 100 SUS neutral solvent-refined lubricating oil. Analysis: Cl, 0.024%w; S, 1.06%w; N, 0.57%w.

Example V—From the monosulfonamide of 1,6-hexanediamine 13.95 g of the sulfonate used in Example 4H and 14.68 g (1.06 mol ratio) of the monosulonamide of 1,6-hexanediamine as prepared in Example 4I are reacted for 44 hours at 175° C. The reaction mass is stripped under a vacuum and sparged with nitrogen to yield 25.43 g of product. The product is diluted with 8.48 g of a 100 SUS neutral solvent-refined lubricating oil. Analysis: Cl, 0.96%w; S, 0.97%w; N, 0.47%w.

Example W—From the monosulfonamide of tris-(2-aminoethyl)amine 23.75 g of o-chlorophenyl polyisobutenylethylsulfonate and 25.0 g (1.04 mol ratio) of the monosulfonamide of tris-(2-aminoethyl)amine as prepared in Example 4K are reacted for 30 hours at 175° C. The reaction product is stripped under vacuum and sparged with nitrogen to yield the product. The product is diluted with a 100 SUS neutral solvent-refined lubricating oil. Analysis: Cl, 0.12%; S, 0.88%w; N, 0.56%w.

EXAMPLE 5

Preparation of the sulfonamides of tetraethylene pentamine (a) To a reaction vessel equipped as in Example 2 is charged 200 ml of ether. To the ether is added dropwise 30 ml of chlorosulfonic acid over a period of 10 minutes. The mixture is sparged with nitrogen and then 300 g of a solution of polybutene, having a number average molecular weight of 950, in 150 ml of ether is added in a fast stream from an addition funnel. The reaction mixture is refluxed for 5 hours, followed by the removal of the majority of the ether solvent by sparging with nitrogen.

The reaction mixture becomes quite viscous. It is diluted with pentane to a volume of 2 liters. Solvent is removed under vacuum at a water-bath temperature of 40°–45° C. and the residue is redissolved in 2 liters of pentane. The solution is filtered through diatomaceous earth and placed in a 3-liter, three-neck flask. While stirring at ambient temperature, 20 ml of dimethyl formamide is added dropwise, followed by the addition of 27.2 ml of thionyl chloride (density 1.655) over a period of 3 minutes. The reaction mixture is stirred for 21 hours, followed by the addition of 10 ml dimethyl formamide and 27.2 ml of thionyl chloride. The reaction mixture is stripped under vacuum at 80° C. and then diluted with xylene to 900 ml, followed by a nitrogen sparge. The product contained 1.58% sulfur and 3.33% chlorine. By titration with KOH the equivalent molecular weight is about 2117.

(b) To 14.6 g of the polyisobutenylsulfonyl chloride prepared in (a) above is added 60 ml pentane and 0.6 g tetraethylene pentamine. The reaction mixture is stirred at room temperature, diluted with pentane and is filtered through diatomaceous earth. The reaction mixture is washed twice with 10 ml of 10% sodium hydroxide and once with 10 ml of water. The mixture is then stripped at 0.1 mm Hg and 100° C. to yield a sulfonamide product having the analysis 1.72, 1.65% sulfur (theory, 1.36%) and 1.33, 1.37% nitrogen (theory, 1.48%).

EXAMPLE 6

Preparation of the sulfonamide from ethyl chlorosulfonate, polyisobutylene and tetraethylene pentamine (a) To a 3-liter reaction flask is charged 750 ml of chlorosulfonic acid. A stirrer, condenser and glass sparge tube are attached to the reaction flask, which is placed in a water bath. The reaction mixture is stirred while ethylene is introduced using a flowmeter to control the flow. A small amount of bubbling occurs at the initial introduction of the ethylene. Then off-gas stops coming over. The reaction vessel is held at this setting until the off-gas comes over very rapidly. The flow of ethylene is then lowered until the off-gas stops. During the reaction of ethylene with chlorosulfonic acid, the temperature of the reaction mixture increases 40° C. over a period of 3½ hours for the total reaction.

The reaction mixture is purified by vacuum distillation to yield 1355 g of ethyl chlorosulfonate boiling at 52°–54° C. overhead (70°–75° C. bottoms) at 20 mm Hg.

(b) To 1640 g of polyisobutylene having a number average molecular weight of 950 in a 5-liter, three-neck flask is added 700 ml of hexane while stirring under a nitrogen atmosphere. To this mixture is added 357 g of ethyl chlorosulfonate prepared in (a) above, while maintaining the temperature below 40° C. The reaction mixture is refluxed for 19 hours at 78°–80° C. The volatile components are removed by stripping, using a rotary evaporator, and then a petroleum hydrocarbon solvent is added and the mixture is stripped again at 90° C. and 10 mm Hg to yield 1840 g of ethyl polyisobutenylsulfonate.

(c) To 1800 g of ethyl polyisobutenylsulfonate in a 5-liter, four-neck flask is added 1 liter of hexane while stirring. To this solution is added a solution of 176.7 g of sodium methoxide in 800 ml of methanol, while maintaining a nitrogen atmosphere and a temperature of 25°–30° C. The reaction mixture is refluxed for 5 hours. The methanol layer is removed. To the remaining solution is added 20 ml of 4.4N methanolic hydrochloric acid. Volatile components are removed by rotary evaporation to yield 1827.4 g of sodium polyisobutenylsulfonate.

(d) To a 5-liter pot is added 1827.4 g of sodium polyisobutenylsulfonate in 600 ml hexane. The reaction mixture is stirred while 209 g of dimethyl formamide is added, followed by the dropwise addition of 189 ml of thionyl chloride while the temperature is maintained below 30° C. The reaction mixture is stirred for 2 hours at room temperature and then diluted wtih 400 ml hexane and allowed to stand for 4 hours. The lower layer is then discarded and the upper layer filtered through Celite 512 and then stripped using a rotary evaporator to yield 1610 g of polyisobutenylsulfonyl chloride.

(e) To a mixture of 68.80 g tetraethylene pentamine and 120 ml dichloromethane in a 2-liter reaction flask while stirring is added a solution of 482.9 g of polyisobutenylsulfonyl chloride in 300 ml methylene chloride, while maintaining the temperature at 25°–30° C. by means of a water bath. The reaction mixture is stirred for one hour at this temperature and then stirred for 16 hours at room temperature, followed by refluxing for ½ hour at 40° C. Eexane is added and the reaction mixture is refluxed at 60° C. for 2 hours.

The reaction mixture is allowed to come to room temperature and then an aqueous saturated solution of potassium carbonate is added. The reaction mixture is stirred for 1 hour, followed by the addition of isopropyl alcohol with stirring for an additional ½ hour.

The supernatart hexane layer is decanted from some sludge-like material and is washed once with water, then filtered through Celite 512 and stripped using rotary evaporation. Toluene is added so that any remaining water can be removed by azeotropic distillation. The reaction product from tetraethylene pentamine and polyisobutylenesulfonyl chloride, primarily the tetraethylene pentamine-derived sulfonamide of polyisobutylenesulfonyl chloride, is added to a neutral solvent-refined petroleum oil having a viscosity of 100 SUS at 100° F., to yield a 50% concentrate of the sulfonamide in the oil. Analysis: 1,48, 1.50%S; 0.026% Cl; 2.09, 2.08% N.

EXAMPLE 7

Oxidation Test

The resistance of an oil composition to oxidative change is measured by the time required for the consumption of 1 liter of oxygen by 100 g of the test oil at 340° F. (171° C.). For convenience, the actual test uses 25 g of oil and the results are corrected to a 100-g sample. A catalyst containing a mixture of soluble salts of iron, copper, lead, tin and manganese is added to the oil. The test is continued for a total of 10 hours and the number of liters of oxygen taken up in this period is also reported. In addition, the viscosity of the oil is measured at the start of the test and at the end of the 10-hour period. The increase is reported as a percentage of the original value. Table I reports the values obtained from subjecting a variety of lubricating oils of this invention to the oxidation test. The base oil used in this test is a solvent-refined neutral hydrocarbon oil having a viscosity of 480 SUS at 100° F. (38° C.) which contains 9 mmols/kg of a zinc dialkyldithiophosphate (8.5%w phosphorus). The test oil also contains 2.5%w nominal actives of the sulfonamide, which is identified by both an example letter and the amine from which it was prepared. For comparison, a reference oil is used containing a commercially available succinimide prepared from tetraethylene pentamine (TEPA) and a polyisobutenylsuccinic anhydride (PIBSA) having a nitrogen content of 2.1%.

The data in Table I show that the viscosity increase for the oils containing the sulfonamides is significantly less than the viscosity increase for the oil containing the commercially available succinimide. It will be noted that this much lower viscosity increase was obtained even though the uptake of oxygen was approximately the same for all test oils.

TABLE I

OXIDATION TEST

| Example 4 Sulfonamide | Amine | Lifetime Hours for One Liter Oxygen Uptake | Total O₂ Uptake Liters/10 hours | $VIS_{100}$ Increase, % |
|---|---|---|---|---|
| G | Piperazine | 3.2 | 5.0 | 29 |
| H | PDA | 3.1 | 4.4 | 17 |
| T | BAPEDA | 2.2 | 5.0 | 30 |
| M | EDA | 2.4 | 5.4 | 32 |
| N | DETA | 2.2 | 5.1 | 37 |
| P | TETA | 2.8 | 4.6 | 30 |
| R | TEPA | 2.7 | 5.2 | 74 |
| Reference | PIBSA/TEPA | 3.1 | 6.1 | 190 |

EXAMPLE 8

Engine Tests

Several of the above sulfonamides were tested in internal combustion engines to demonstrate their usefulness as lubricating oil additives.

One such internal combustion engine test is the severe Ford V-8 piston varnish test. In this test, a Ford V-8 engine of 302-inch³ displacement is cycled through idle/cold/hot cycles at an RPM of 500/2500/2500 at water temperatures of 115/125/170° F., and a gallery temperature of 120/170/205° F. for periods of 45/120/75 minutes, respectively. In this test procedure, the engine is disassembled at 20-hour intervals and piston varnish is measured on a scale of 0 to 10, with 10 being completely clean.

The base oil for test tests was a mid-continent base stock SAE 30 oil, containing 30 mmols/kg of a carbonated, sulfurized calcium polypropylene phenate, 30 mmols/kg of a carbonated calcium sulfonate and 15 mmols/kg of mixed zinc dithiophosphates. From this reference oil, lubricating oils were prepared by adding the various sulfonamides, which are identified in Table II in the same manner as in Example 7.

Table II shows the results of testing these sulfonamides. For comparison, a reference is included which contains no dispersant and also references which contain the same succinimide used in Example 7 above.

TABLE II

PISTON VARNISH TEST

| Sulfonamide | | Quantity in Oil | | | Piston Varnish Rating at Hrs. | | |
|---|---|---|---|---|---|---|---|
| Example 4 | Amine | %w | %w N | mmols /kg S | 40 | 60 | 80 |
| None[1] | — | — | — | — | 7.2 | 6.9 | — |
| T | BAPEDA | 3.0 | 0.81 | 9 | 9.5 | 8.5 | 7.7 |
| L | EDA | 2.2 | 0.025 | 9 | 7.9 | 7.2 | — |
| N | DETA | 2.2 | 0.034 | 9 | 9.2 | 8.2 | 7.8 |
| R[1] | TEPA | 3.0 | 0.093 | 11 | 9.6 | 9.4 | 9.2 |
| Q | TBPA | 4.6 | 0.083 | 9 | 9.3 | 8.5 | 8.3 |
| Reference[2] | PIBSA/TEPA | 3.0 | 0.063 | | 8.7 | 7.9 | 7.3 |
| Reference II[2] | PIBSA/TEPA | 6.0 | 0.126 | | 9.6 | 9.2 | 8.9 |

[1]Average of 2 tests
[2]Average of 8 tests

From the above data, it can be seen that the sulfonamide prepared from tetraethylenepentamine is a better dispersant than the succinimide prepared from the same amine. It can also be seen that the sulfonamides prepared from the various amines all function quite well as dispersants in this varnish test.

EXAMPLE 9

1-G Caterpillar Test

Another such test is the well-known 1-G Caterpillar test in which a single-cylinder diesel engine having a 5⅛ inch bore by 6¼ inch stroke is operated under the following conditions: timing, degrees ETCC 8; brake mean effective pressure, psi 141; brake horsepower 42; Etu's per minute 5850; speed 1800 RPM; air boost, 53 inch Hg absolute, air temperature in, 255° F.; water temperature out, 190° F.; and sulfur in fuel, 0.4%w. At the end of each 12 hours of operation, sufficient oil is drained from the crankcase to allow addition of 1 quart of new oil. In the test on the lubricating oil compositions of this invention, the 1-G test is run for 60 hours. At the end of the 60-hour period, the engine is dismantled and rated for cleanliness. The ring lands are rated on a scale of 0 to 800, with 0 representing clean and 800 representing black deposits. The ring grooves are rated on a scale of 0 to 100 groove fill, with 0 representing clean. The underhead of the piston is rated on a scale of 0 to 10, with 0 representing dirty and 10 representing clean.

The base oil used in these tests is a mid-continent base stock SAE 30 oil containing 12 mmols/kg of a zinc bis(alkylaryl) dithiophosphate and the sulfonamide which is identified in Table III in the same manner as they were identified in Example 8. For comparison, oils containing no dispersant and the same commercially available succinimide as used in Example 8 were tested.

As in the engine varnish test, it can be seen that the sulfonamides prepared from the various amines function quite well as dispersants. It should also be noted that several of the sulfonamides were used at about one-half the nitrogen concentration of that used for the commercially available succinimide and yet the oil provided approximately comparable dispersancy performance.

TABLE III

60-HR 1-G CATERPILLAR TEST

| Sulfonamide | | Quantity in Oil | | | | | |
|---|---|---|---|---|---|---|---|
| Example 4 | Amine | %W | %W N | mmols/Kg S | Lands | Grooves | Underhead |
| None | — | — | — | — | 750-780-765 | 81-16-7-8 | 5.7 |
| G | Piperazine | 2.2 | 0.024 | 11 | 477-84-20 | 73-16-1-1 | 1.4 |
| H | PDA | 2.4 | 0.027 | 11 | 275-30-20 | 38-12-1-1 | 2.8 |
| M | EDA | 2.8 | 0.035 | 14 | 390-25-20 | 43-5-1-0 | 4.5 |
| L | EDA | 2.3 | 0.026 | 10 | 460-45-20 | 40-9-1-0 | 1.9 |
| N | DETA | 2.5 | 0.040 | 10 | 435-70-35 | 48-4-1-1 | 2.3 |
| P | TETA | 6.2 | 0.074 | 24 | 220-160-60 | 42-5-1-1 | 0.8 |

TABLE III-continued

| Sulfonamide Example 4 | Amine | 60-HR 1-G CATERPILLAR TEST Quantity in Oil | | | Lands | Grooves | Underhead |
|---|---|---|---|---|---|---|---|
| | | %W | %W N | mmols/Kg S | | | |
| Reference I | PIBSA/-TEPA[1] | 3.5 | 0.74 | — | 390-50-35 | 40-8-1-0 | 3.1 |

[1]Average of 3 tests

What is claimed is:

1. A process for preparing an oil-soluble, nitrogen-containing composition comprising combining, at a temperature from about 50° C. to about 250° C., an aryl ester of a substantially saturated hydrocarbylethylsulfonic acid, the substantially saturated hydrocarbyl substitutent containing at least 20 aliphatic carbon atoms, with from 0.1 to 15 mols, per equivalent of said ester, of a nitrogen-containing compound containing at least one—NH function.

2. The process of claim 1 wherein the aryl ester is selected from those of the formulas

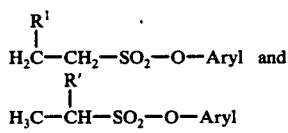

wherein
 (a) $R^1$ represents a substantially saturated hydrocarbyl containing from about 20–350 carbon atoms and 0–3 sites of olefinic unsaturation, and
 (b) Aryl represents an aryl radical or a substituted aryl radical; and
 (c) the amine has the formula $$H-N-R^3$$
$$\phantom{H-N-}|$$
$$\phantom{H-N-}R^2$$

in which $R^2$ and $R^3$ (A) each independently represent hydrogen, hydrocarbyl, alicyclic hydrocarbyl or alkylene polyamine hydrocarbyl or (B) together represent the remainder of a heterocyclic amine.

3. A process for preparing an oil-soluble, nitrogen-containing composition comprising combining an alkyl chlorosulfonate wherein the alkyl portion contains from 1 to 4 carbon atoms, and an olefinically unsaturated hydrocarbon compound containing at least 20 carbon atoms to form alkyl hydrocarbylsulfonate, treating with an alcoholic solution of an alkali metal hydroxide to form the alkali metal hydrocarbylsulfonate, treating said alkali metal hydrocarbylsulfonate with a chlorinating agent to form a hydrocarbylsulfonyl chloride, and combining the hydrocarbylsulfonyl chloride with 0.1 to 15 mols per mol of hydrocarbylsulfonyl chloride, of a nitrogen-containing compound containing at least one—NH function.

* * * * *